United States Patent
Ogawa et al.

(10) Patent No.: US 6,733,987 B2
(45) Date of Patent: May 11, 2004

(54) METHOD FOR CUTTING A BIOLOGICAL SAMPLE AND A DEVICE USED THEREFOR

(75) Inventors: Masashi Ogawa, Tokyo (JP);
Masatoshi Takahashi, Kanagawa (JP);
Kazuko Hanai, Kanagawa (JP);
Hiroshi Arakatsu, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 159 days.

(21) Appl. No.: 10/045,539

(22) Filed: Oct. 26, 2001

(65) Prior Publication Data

US 2002/0142412 A1 Oct. 3, 2002

(30) Foreign Application Priority Data

Oct. 31, 2000 (JP) ........................................ 2000-332252

(51) Int. Cl.$^7$ .............................. G01N 1/44; G01N 1/28
(52) U.S. Cl. ................. 435/40.52; 435/40.51; 435/40.5; 435/6
(58) Field of Search ........................ 435/40.51, 40.52, 435/40.5, 6

(56) References Cited

U.S. PATENT DOCUMENTS 5,985,085 A * 11/1999 Baer et al. ................. 156/285

OTHER PUBLICATIONS

Schütze et al (Cellular and Molecular Biology 44(5):735–746 (1998)).*
Emmert–Buck, et al., "Laser Capture Microdissection," *Science*, vol. 274, pp. 998–1001 (1996).
Bonner, et al. "Laser Capture Microdissection: Molecular Analysis of Tissue" *Science*, vol. 278, pp. 1481, 1483 (1997).
Furukawa, et al. Microarray SNP Pharmacogenomics Gene, vol. 18(12):119–124 (2000).
Schutze, et al. "Identification of expressed genes by laser–mediated manipulation of single eells", *Nature Biotechnology*, vol. 16, pp. 737–742 (1988).
Patent Database Search Results (Searching 1976–2000).

* cited by examiner

*Primary Examiner*—Francisco C Prats
(74) *Attorney, Agent, or Firm*—Reed Smith LLP

(57) ABSTRACT

An object of the present invention is to provide a method which comprises adhering a biological sample to a film, cutting out a target area of the sample, and then peeling off the film to collect the fragment which was cut out, wherein the operability is good and a cutting sharpness in cutting by a laser beam is good. The present invention provides a method for cutting a biological sample by light irradiation, which comprises locating the biological sample and a colored film having a thickness of 3 to 6 $\mu$m onto one side of a support, and irradiating the biological sample with a light beam, thereby cutting out a target area of the biological sample.

7 Claims, 1 Drawing Sheet

Sample:Mouse Testis

After microdissection

Sample collected by microdissection
(350μm×150μm)

METHOD FOR CUTTING A BIOLOGICAL SAMPLE AND A DEVICE USED THEREFOR

CROSS-REFERENCES TO RELATED APPLICATIONS

This application claims priority of Japanese Application Nos. 332252/2000 filed Oct. 31, 2000, the complete disclosure of which is hereby incorporated by reference.

FIELD OF THE INVENTION

The present invention relates to a method for cutting a biological sample and to a device used therefor. More specifically, the present invention relates to a method for cutting a target area of a biological sample by irradiating the biological sample with a light beam, and a device used therefor.

BACKGROUND OF THE INVENTION

A microarray technique involves hybridizing DNAs spotted on a glass slide with labelled probes prepared from RNA extracted from tissues or cells to be examined, detecting the generated signal, and then measuring the intensity of the signal to determine relative expression levels of genes corresponding to the hybridized spots. Advances in the development of such a microarray technique enable us to assay numerous genes (several thousands to several tens of thousands of genes) at a time for their expression levels. This technique can be used to exhaustively examine a disease associated with multiple abnormal genes, such as cancer or leukemia in order to identify a gene or genes abnormally expressed in such diseases. In a study aimed at determining a cause and a development mechanism of such diseases, it is important to extract only a specific type of cell from a biological sample.

For example, in molecular studies of human tumors, a quantitative or qualitative evaluation of the expression of a protein or nucleic acid in human tumor cells is necessary. In these studies, it is necessary that tumor cells are distinguished and separated from normal cells, and the expression levels of a target nucleic acid or protein are analyzed and compared in each type of the cells.

However, invasive tumor tissues contain many types of cells (e.g., tumor cells, stroma cells, endothelial cells, normal epithelial cells and inflammatory cells). In order to accurately perform a quantitative or qualitative evaluation on the expression of a protein or nucleic acid in tumor cells, it is necessary that only tumor cells are collected from many types of cells contained in tumor tissues. To this end, it is necessary that a biological sample is cut at a target position.

As a method for cutting a biological sample (e.g., living tissue fragments, cells, chromosomes and microorganisms) at a target position and collecting the cut sample, a method of irradiating laser beam on a sample for cutting and collecting the sample is known (laser capture microdissection; Emmert-Buck, M. R. et al., Science 274, 998–1001, 1996 and Bonner, R. R. et al., Science, 278, 1481–1482, 1997). This method involves adhering a biological sample to a film, cutting out a target area of the sample, and then peeling off the film to collect the fragment which was cut out. However, such a conventional method presents a problem of difficulty in operation, in particular, difficulty in locating a film on a support, due to a low film thickness. Also, the conventional method should be improved to give a better cutting (i.e., better sharpness) in cutting by a laser beam.

SUMMARY OF THE INVENTION

An object of the present invention is to provide a novel method for cutting out a target area of a biological sample (e.g., living tissue fragments, cells, chromosomes and microorganisms) and collecting the cut sample. That is, an object of the present invention is to provide a method which comprises adhering a biological sample to a film, cutting out a target area of the sample, and then peeling off the film to collect the fragment which was cut out, wherein the operability is good and a cutting sharpness in cutting by a laser beam is good.

As a result of diligent efforts to achieve the above object, the present inventors have found that a superior method for cutting a biological sample at a target position, which achieves the above-mentioned objects, can be provided by using a colored film having a thickness of 3 to 6 $\mu$m to which the biological sample is adhered. The present invention was completed based on this finding.

Thus, according to the present invention, there is provided a method for cutting a biological sample by light irradiation, which comprises locating the biological sample and a colored film having a thickness of 3 to 6 $\mu$m onto one side of a support, and irradiating the biological sample with a light beam, thereby cutting out a target area of the biological sample.

The present invention also relates to a method for cutting and collecting a biological sample, which further comprises collecting the sample which was cut.

According to another aspect of the present invention, there is provided a device for cutting a biological sample, wherein a colored film having a thickness of 3 to 6 $\mu$m is located on one side of a support.

DETAILED DESCRIPTION OF THE INVENTION

Figure 1:
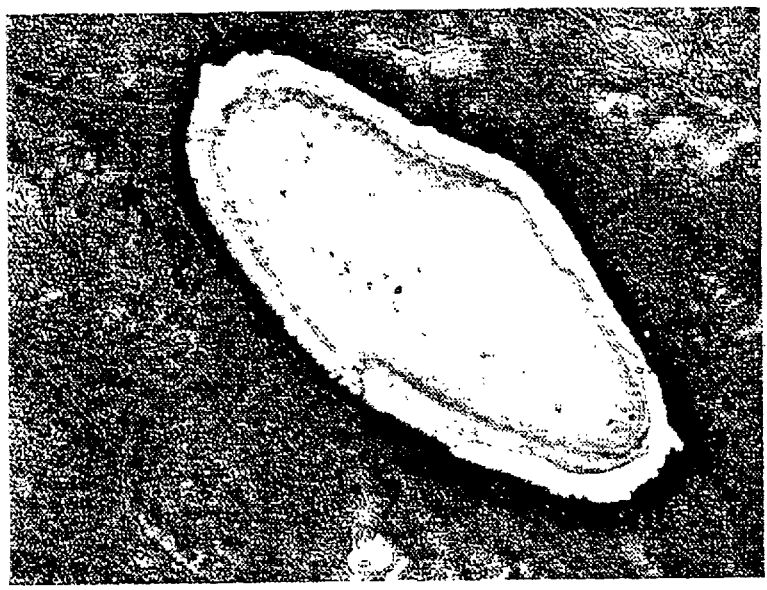
FIG. 1 shows a result where mouse testis sample was collected by microdissection technique.
Figure 1:
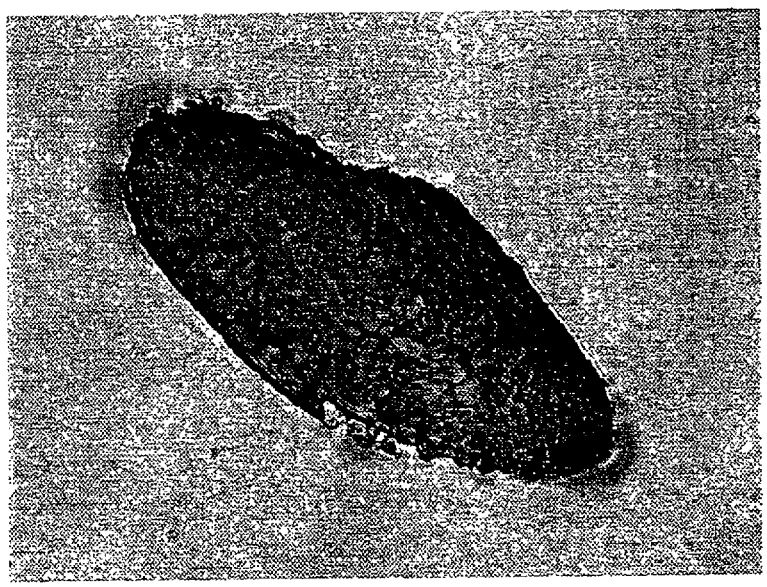

The embodiment of the present invention will be described below in more detail.

The method for cutting a biological sample by light irradiation according to the present invention is characterized by locating the biological sample and a colored film having a thickness of 3 to 6 $\mu$m onto one side of a support, and irradiating the biological sample with a light beam, thereby cutting out a target area of the biological sample.

In the present invention, the biological sample may be irradiated with a light beam from the other side of the support which is opposite to the side holding the biological sample. Alternatively, the biological sample may be irradiated with a light beam from the same side of the support as the side holding the biological sample, after the support folding the biological sample is inverted.

A biological sample used in the present invention may be of any origin, so long as it is derived from a living organism. Examples include living tissue fragments, cells, chromosomes or microorganisms. For example, a biological sample containing a diseased lesion (e.g., cancer) may be used in the method of the present invention. In this case, diseased cells (e.g., cancer cells) can be separated and collected from normal cells by the present invention.

A light beam used in the present invention may preferably be a laser beam because a laser beam can be readily and effectively focused on a small area on a given surface. The wavelength of a laser beam usually ranges from about 150 nm to about 10,000 nm, with an ultraviolet laser beam having a wavelength of 180 nm to 400 nm being particularly preferred. In a case where a laser beam is used, its beam diameter should be set appropriately depending on the type and thickness of the biological sample, and it generally ranges from about 1 μm to about 50 μm. Also, its beam intensity may be appropriately adapted to the type and thickness of the biological sample and/or area size to be cut out. For example, the beam intensity may be set at about 0.5 $J/cm^2$ to about 3.0 $J/cm^2$ when tissue fragments are used as a biological sample, and about 0.1 $J/cm^2$ to about 3.0 $J/cm^2$ when cells are used, and about 0.01 $J/cm^2$ to about 3.0 $J/cm^2$ when chromosomes or microorganisms are used.

A support used in the present invention may be of any type, so long as it allows light to pass therethrough. A preferred support is a transparent support, including a glass support (glass slide or cover slip) and a polyethylene terephthalate support.

A colored film used in the present invention is characterized by having a thickness of 3 μm to 6 μm. A film having a thickness of less than 3 μm is not preferred because it lacks operability and provides difficulty in locating it onto a support, while a film having a thickness of greater than 6 μm is not preferred because it provides difficulty in cutting a sample by light irradiation. The present invention is characterized by the use of a colored film, not a transparent film. This takes advantage of the benefit that a colored film facilitates the cutting by light irradiation.

Specific examples of a colored film which can be used in the present invention include a yellow aramid film. Examples of such aramid film includes a polymer of terephthalic acid and p-phenylenediamine (p-phenylene terephthalamide, also referred to as PPTA) (for example, Kevlar®, Twaron®, or Technora®).

A colored film such as an aramid film may be prepared in a known manner. For example, an aramid polymer is dissolved in concentrated sulfuric acid and the resulting dope is degassed. Next, the degassed dope is casted through a die having an appropriate-sized slit onto a mirror-polished belt made of tantalum, treated with air blow to make it optically isotropic, and then solidified by guiding it into aqueous sulfuric acid along with the belt. At this time, the film itself may also be provided with capping. Next, the solidified film is peeled off from the belt, and then sequentially passed through and washed in warm water, aqueous solution of sodium carbonate, and then water at 25° C. The washed film having a water content of about 280% is first uniaxially stretched in the longitudinal direction (MD) at room temperature by using roll peripheral speed differential, and then introduced into a tenter where the film is stretched in the transverse direction (TD) in a section near the tenter inlet, heated and dried every given length at 150° C. in the midsection of the tenter, and further heat-treated at 400° C. using an infrared lamp mounted near the tenter outlet. The treated long film is wound up to give a PPTA film.

In the method of the present invention, a colored film having a thickness of 3 to 6 μm may be located on one side of a support, and a biological sample may be located on the film, thereby giving a configuration comprising the support, colored film and biological sample in order of bottom to top; or a biological sample may be located on one side of a support, and a colored film having a thickness of 3 to 6 μm may be located on the sample, thereby giving a configuration comprising the support, biological sample and colored film in order of bottom to top. The former configuration is preferred in the present invention.

The present invention also provides a device for cutting a biological sample, wherein a colored film having a thickness of 3 to 6 μm is located on one side of a support.

To cut out a target area of a biological sample in the method of the present invention, the biological sample may be preferably stained in a suitable method.

A biological sample which can be used in the present invention may be stained with, for example, hematoxylin and eosin, thereby enabling a specific cell population to be distinguished under microscopic visualization and enabling target cells to be isolated and collected from the entire tissue.

In the method of the present invention, the cutting out of a target area may be preferably performed under microscopic view.

More specifically, in the method for cutting a biological sample according to the present invention, a transparent support holding a colored film and a biological sample (containing target cells to be collected) on the upper side may be located on the microscope stage, and a target area of the biological sample is then determined through the transparent support while observing the sample through the microscope eyepiece or monitoring an image taken by a CCD camera. The determination of a target area may be performed by dye staining or immunological staining techniques.

Next, a light beam is generated from an irradiation means such as a laser irradiator, preferably an ultraviolet laser irradiator. The beam is then focused to a small diameter and applied to the biological sample, preferably from the bottom side of the support, along a target position on the biological sample, thereby cutting out the biological sample. Focusing the laser beam on the optical center of the optical microscopic field allows activation energy to be concentrated to an area of the colored film in contact with the biological sample. Also, the duration of laser irradiation may be adjusted appropriately in such a manner that a required amount of energy is directed to a target area to be cut out.

Furthermore, the present invention relates to a method for cutting and collecting a biological sample, which comprises cutting the biological sample by the cutting method mentioned above, and then collecting the sample which was cut out.

When a sufficient amount of energy from the laser beam is absorbed in the surface of the colored film in contact with target cells in the biological sample, an adhesive layer is formed between the colored film and the target cells. Thus, by removing the film, the target cells can be separated and collected from the rest of the biological sample.

The size of a sample to be separated and collected may be changed depending on the light beam (preferably, laser beam) diameter and pulse duration. According to the method of the present invention, a sample of small size (about 1 μm to about 100 μm) can be collected. In addition, a laser beam can be focused on an area smaller than a single cell diameter, thereby permitting the separation and collection of only a single target cell or a part thereof.

The thus cut sample may be collected in any manner. For example, the laser beam irradiated for cutting the sample may be shifted away from its optimal lens focus to give an extended beam diameter for energy scattering, thereby peeling off and blowing upward the cut sample from the support without cutting a section. Thus, the sample peeled off from the support can be collected in a container such as a microtube cap.

Examples of a device which can be used to carry out the method for cutting a biological sample according to the present invention include a CRI-337 Laser Scissors™ 337/120 module (Cell Robotics Inc., USA).

The thus cut and collected target sample may be stored in solution, and may be subjected to an analysis. In a case where DNA or RNA contained in target cells is analyzed, the collected sample may be subjected to polymerase chain reaction (PCR), followed by a standard gene analysis such as Southern blotting hybridization, Northern blotting hybridization, dot blotting hybridization or sequencing.

For example, mRNA may be extracted from the collected sample by using column chromatography on oligo-dT. The mRNA collected from target cells may further be amplified by RT-PCR, and the amplified products can be further analyzed.

In a case where a specific protein or polypeptide contained in target cells is analyzed, the collected sample may be subjected to, for example, enzyme assay using a labelled substrate, immunoassay using a labelled antibody, and/or biochemical assay.

The present invention will be further described in the following examples. The examples are provided for illustrative purposes only, and are not intended to limit the scope of the invention.

EXAMPLES

Example 1

Microdissection According to the Method of the Present Invention (1) Preparation of Aramid Film An aramid film as a non-magnetic film was prepared in a known manner mentioned below. PPTA polymer having an inherent viscosity ($\eta_{inh}$) of 5.5 was dissolved in concentrated sulfuric acid containing 0.005% by weight of colloidal silica (80 nm in average diameter) to give a polymer concentration of 11.5%, and the dope was then degassed under vacuum while maintaining this dope at about 70° C. The degassed dope was casted at a discharge line speed of 3.5 m/min through a die having a 0.15 mm×300 mm slit onto a mirror-polished belt made of tantalum (moving at a speed of 12 m/min), treated with air blow at about 90° C. under a relative humidity of about 85% to make it optically isotropic, and then solidified by guiding it into 15% by weight of aqueous sulfuric acid at ±5° C. along with the belt. At this point, the film itself can be provided with capping. Next, the solidified film was peeled off from the belt, and then sequentially passed through and washed in warm water at about 40° C., 1% aqueous sodium carbonate and then water at 25° C. The washed film having a water content of about 280% was first uniaxially stretched 1.2 times its original length in the longitudinal direction (MD) at room temperature by using roll peripheral speed differential, and then introduced into a tenter where the film was stretched 1.2 times its original width in the transverse direction (TD) in a section near the tenter inlet, heated and dried every given length at 150° C. in the midsection of the tenter, and further heat-treated at 400° C. using an infrared lamp mounted near the tenter outlet. The treated long film was wound up. The resulting PPTA film had a good transparency and a thickness of 3.8 $\mu$m or 4.2 $\mu$m.

(2) Preparation of Sample to be Cut

The aramid film prepared in Example 1 (2 cm×2 cm; 3.8 $\mu$m or 4.2 $\mu$m in thickness) was located onto a glass slide which allows a laser beam having a wavelength of 377 nm to pass therethrough, and then adhered to the slide using Nail Polish.

A mouse testis tissue was transferred to a plastic freezing container (e.g., Cryomond, MILES) and embedded in an O.C.T. compound (Sakura Seiki, Co., Ltd.). The tissue sample was frozen under liquid nitrogen for about 30 seconds to about 40 seconds. The frozen sample was sliced into about 8 $\mu$m sections in a frozen section-producing device (cryostat). Each of the sliced sections was directly adhered onto the film-holding glass slide prepared above.

The glass slide to which the frozen section was adhered, was stained with hematoxylin and eosin (HE) in a general manner ("Overall Information on Staining," starting on page 2, 1988, published by Ishiyaku Pub., Inc.). Mayer's hematoxylin solution (Wako Pure Chemical Industries, Ltd.) and a 1% eosin solution (Wako Pure Chemical Industries, Ltd.) were used as hematoxylin and eosin, respectively.

(3) Cutting of Sample by Laser

The sample on the glass slide was cut at a target position using an LS-337 Laser Scissors™ 337/120 module (included in CRI-337 system; Cell Robotics Inc., USA) under microscopic view (microdissection). Conditions for microdissection are presented below:

Nitrogen-excited pulse laser

Wavelength: 337 nm

Power: 1 to 120 $\mu$J per pulse (variable) (about 80 $\mu$J/pulse for cutting because the cutting is carried out at a level of 65% to 80% and at 100 pps)

Subsequently, the laser beam was shifted downward from its optimal lens focus to give an extended beam diameter for energy scattering, thereby peeling off and blowing upward the cut section from the glass slide. The cut out section was collected in a microtube cap.

FIG. 1 shows the sample before and after microdissection, as well as the target area which was cut out and collected from the sample. As shown in FIG. 1, according to the method of the present invention, a target area on tissue could be successfully cut out and collected.

Example 2

Comparison Between the Method of the Present Invention and Comparative Examples

The same procedures as stated in Example 1 were repeated to locate a biological sample onto a glass slide and carry out microdissection on the sample, except that the material and thickness of a film to be held on the glass slide were varied as shown in Table 1 below.

Table 1 shows the results of the evaluation on adhesion suitability to glass slide (operability), microdissection suitability, and cutting sharpness (sharp cut), each of which is expressed by one of the following three ranks: ○, Δ and X.

TABLE 1

| | Thickness ($\mu$m) | | | |
| --- | --- | --- | --- | --- |
| | 1.0 | 3.6 | 4.2 | 7.4 |
| | Material | | | |
| | PET (transparent) | Aramid (yellow) | Aramid (yellow) | PET (transparent) |
| Adhesion suitability to glass slide | X | Δ | ○ | ○ |
| Microdissection suitability | ○ | ○ | ○ | X |
| Cutting sharpness (sharp cut) | Δ | ○ | ○ | X |
| Remarks | Control | Invention | Invention | Control |

The results of Table 1 shows that the present invention is superior to the control examples.

According to the present invention, it has become possible to provide a method which comprises adhering a biological sample to a film, cutting out a target area of the sample, and then peeling off the film to collect the fragment which was cut out, wherein the operability is good and a cutting sharpness in cutting by a laser beam is good.

The contents of the specification of Japanese Patent Applications No. 2000-332252, based on which the present application claims priorities, are hereby incorporated in their entirety into the disclosure of the present specification.

What is claimed is:

1. A method for cutting a biological sample by light irradiation, which comprises locating the biological sample and a colored film having a thickness of 3 to 6 μm onto one side of a support, and irradiating the biological sample with a light beam, thereby cutting out a target area of the biological sample, wherein said light beam is an ultraviolet laser beam and the colored film is an aramid film.

2. The method according to claim 1 wherein the biological sample is irradiated with a light beam from the other side of the support which is opposite to the side holding the biological sample.

3. The method according to claim 1, wherein the biological sample is living tissue fragments, cells, chromosomes or microorganisms.

4. The method according to claim 1, wherein the support is a glass support.

5. The method according to claim 1, wherein the colored film having a thickness of 3 to 6 μm is located on one side of the support and the biological sample is located on the film.

6. The method according to claim 1, wherein the cutting out of a target area is carried out under microscopic view.

7. A method for cutting and collecting a biological sample, which comprises cutting out the biological sample by the method according to claim 1, and then collecting the sample that was cut out.

* * * * *